(12) United States Patent
Palti

(10) Patent No.: US 11,197,971 B2
(45) Date of Patent: Dec. 14, 2021

(54) NANOTUBE-BASED HUMIDIFICATION

(71) Applicant: Yoram Palti, Haifa (IL)

(72) Inventor: Yoram Palti, Haifa (IL)

( * ) Notice: Subject to any disclaimer, the term of this patent is extended or adjusted under 35 U.S.C. 154(b) by 384 days.

(21) Appl. No.: 16/541,436

(22) Filed: Aug. 15, 2019

(65) Prior Publication Data

US 2020/0054853 A1 Feb. 20, 2020

Related U.S. Application Data

(60) Provisional application No. 62/719,365, filed on Aug. 17, 2018.

(51) Int. Cl.
| | |
|---|---|
| *A61M 16/16* | (2006.01) |
| *A61M 16/10* | (2006.01) |
| *F24F 11/74* | (2018.01) |
| *F24F 6/04* | (2006.01) |
| *F24F 110/20* | (2018.01) |
| *F24F 110/10* | (2018.01) |

(52) U.S. Cl.
CPC .......... *A61M 16/109* (2014.02); *F24F 6/04* (2013.01); *F24F 11/74* (2018.01); *A61M 2205/3327* (2013.01); *A61M 2205/3368* (2013.01); *F24F 2110/10* (2018.01); *F24F 2110/20* (2018.01)

(58) Field of Classification Search
CPC ........ A61M 16/109; A61M 2205/3327; A61M 2205/3368; A61M 16/16; A61M 16/161; F24F 6/04; F24F 11/74; F24F 2110/10; F24F 2110/20
USPC .............. 261/128, 129, 135, 142, 146, 23.1; 128/203.25, 203.26, 203.27, 204.13
See application file for complete search history.

(56) References Cited

U.S. PATENT DOCUMENTS 9,138,522 B2 9/2015 Palti
9,827,534 B2 11/2017 Palti
(Continued)

FOREIGN PATENT DOCUMENTS

JP 2016113308 A 6/2016
WO 2017109737 A1 6/2017

OTHER PUBLICATIONS

American Association for Respiratory Care, "AARC Clinical Practice Guideline: Oxygen therapy for adults in the acute care facility—2002 revision and update," Respiratory Care 2002, 47(6), 717-720.
(Continued)

*Primary Examiner* — Charles S Bushey
(74) *Attorney, Agent, or Firm* — Potomac Law Group, PLLC

(57) ABSTRACT

A humidifier uses a field of hydrophobic, nanotubes (e.g., vertically aligned carbon nanotubes) to humidify a gas. Voids in the field form liquid flow channels that are wide enough for liquid water to pass through. The nanotubes are spaced close enough to each other to prevent the water from escaping the channels. Water in the channels is absorbed by gas that flows and/or diffuses between the nanotubes. Humidity levels in the gas can be measured and controlled to a desired level by controlling the rate of flow of gas through the humidifier, controlling heating of the gas, and/or adjusting the total area of molecular transfer from the water to the gas by providing multiple banks of nanotubes and controlling the number of banks through which the gas flows.

17 Claims, 6 Drawing Sheets

(56) References Cited

U.S. PATENT DOCUMENTS

2014/0088725 A1* 3/2014 Palti .................. A61M 1/32
 623/23.65
2016/0184547 A1* 6/2016 Leonard ............. A61M 16/20
 128/203.25

OTHER PUBLICATIONS

Chalon et al., "Effect of dry anaesthetic gases on tracheobronchial epithelium," Anaesthesiology, vol. 37, p. 338, 1972.
Conway, "The effects of humidification for patients with chronic obstructive airways disease," Physiotherapy, 78(2), p. 97-101, 1992.
Dery, "The evolution of heat and moisture in the respiratory tract during anaesthesia with a non-rebreathing system," Canadian Anaesthesia Society Journal, vol. 20, p. 269, 1972.
Dreyfuss, "Prospective study of nosocomial pneumonia and of patient and circuit colonisation during mechanical ventilation with circuit changes every 48 hours versus no change," American Rev. Respiratory Disease, vol. 43, p. 738-43, 1991.
International Search Report and Written Opinion issued in application No. PCT/IB2019/056934 dated Dec. 18, 2019.
Jackson et al., "An evaluation of the heat and moisture exchange performance of four ventilator circuit filters," Intensive Care Medicine, vol. 18, p. 264-268, 1992.
Jackson, "Humidification in the upper respiratory tract: a physiological overview," Intensive and Critical Care Nursing, vol. 12, p. 27-32, 1992.
Li et al., "Transfer of vertically aligned carbon nanotube arrays onto flexible substrates for gecko-inspired dry adhesive application," RSC Advances, Issue 58, May 2015.
Ping et al., "Vertically aligned carbon nanotube arrays as a thermal interface material," APL Mater, vol. 7, 020902, Feb. 2019.
Rhame, "Bubbling humidifiers produce microaerosols which can carry bacteria," Infection Control, 7(8), p. 403-407, 1986.
Strobl et al., "c-VACNT (TM) enabled Fluid Reactor Innovations: a NanotoMacro (TM) transformation," CVD Equipment Corporation, poster, Jun. 2019.
Mllafane, "Gradual reduction of endotracheal tube diameter during mechanical ventilation via different humidification devices," Anaesthesiology, vol. 85, pp. 1341-1349, 1996.

* cited by examiner

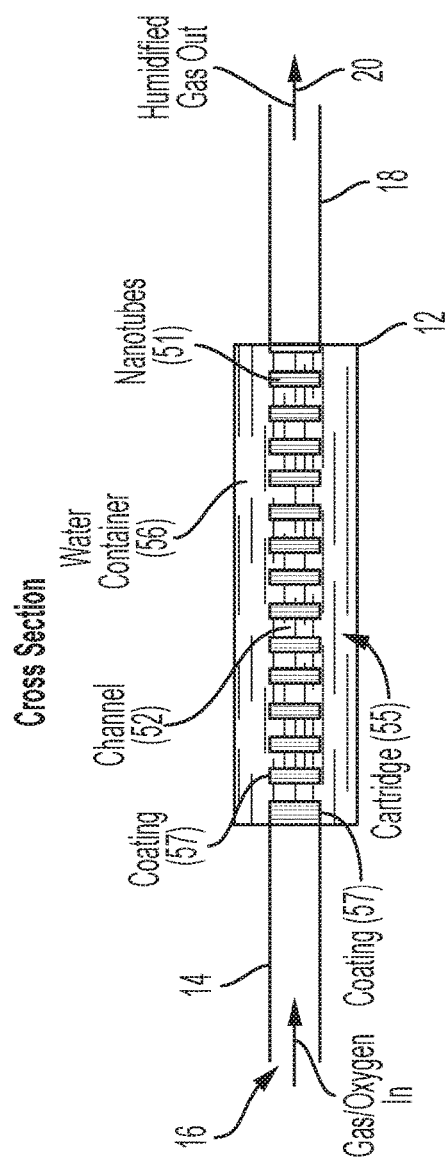

NANOTUBE-BASED HUMIDIFICATION

CROSS REFERENCE TO RELATED APPLICATIONS

This Application claims the benefit of U.S. Provisional Application 62/719,365 filed Aug. 17, 2018, which is incorporated herein by reference in its entirety.

FIELD OF THE INVENTION

This application is directed to humidification of gases. Such gases may be used, for example, in respiratory assist devices and mechanical ventilation.

BACKGROUND

Humidification of inhaled gases has been the standard of care in both respiratory assist devices and mechanical ventilation for a long period of time. When a patient receives a supplemental medical gas (e.g., oxygen), it is generally cool and dry and can cause drying of the secretions and mucosa, potentially leading to airway obstruction and tissue injury. This problem arises from the fact that oxygen and other gas types, whether originating from central hospital supplies, portable gas tanks or air oxygen concentrators, provide practically pure gas, i.e., without any water content. Inspiration of gas with low humidity results in the patient's secretions becoming more viscous. These secretions can gradually build up such that the effective diameter of the tracheal tube and the airways decreases, the resistance to gas flow increases, increasing the work of breathing. In extreme cases, occlusion can occur. Furthermore, inspiration of dry gas for extended periods of time may lead to squamous metaplasia of the trachea.

To overcome these issues, a number of technologies designed to humidify and heat the gas to appropriate levels have been developed and introduced. Such humidifiers are an integral part of many respiratory assist systems as well as respirators. It has been shown that delivering at least 31 mg $H_2O/L$ (air) as measured at the pharynx, will avoid mucosal drying in a healthy adult. Ideally, inspired gas should be humidified to 37° C. and 44 mg $H_2O/L$. This ensures patient comfort and promotes respiratory health by optimizing mucocilliary function and the clearance of secretions.

There are several types of humidifiers, i.e., devices that, in the context of respiratory assist devices, add molecules of water to gas. They are classified as active or passive. Active humidifiers are based on the presence of external sources of heat and water, while passive humidifiers utilize the patient's own temperature and hydration. Active humidifiers act by allowing air passage inside a water reservoir that may be heated. Examples of conventional active humidifiers include bubble humidifiers, pass-over humidifiers, counter-flow humidifiers, and in-line vaporizers. Many humidifiers are also equipped with filters to prevent particles and bacteria, etc. from entering the patient's respiratory systems.

In bubble humidifiers, gas is forced down a tube into the bottom of a water container. The gas escapes from the distal end of the tube under water surface forming bubbles, which gain humidity as they rise to the water surface. Some of these humidifiers have a diffuser at the distal end of the tube that breaks gas into smaller bubbles. The smaller the bubbles, the larger the gas-water interface, allowing for higher water vapor content in the produced gas. Other factors that influence water vapor content of the produced gas are the height of water in the container and the flow rate.

A problem with bubble humidifiers is that they exhibit high resistance to airflow, imposing higher work of breathing than pass-over humidifiers. Furthermore, bubble humidifiers may generate micro-aerosols that may be associated with direct transmission of infection from the humidifier to the patient's lungs. Water particles 1-5 microns in diameter are particularly dangerous as they can reach the distal air spaces where pulmonary clearance mechanisms may not be efficient, and they can carry significant numbers of viable bacteria.

As for heating systems for humidifiers, conventional approaches include a hot plate that sits at the bottom of the humidifier; a wraparound element that surrounds the humidifier chamber; a collar element that sits between the reservoir and the outlet; an immersion heater, which is placed directly inside the water reservoir; and a heated wire, which is placed in the inspiratory limb of the ventilator. Filters are often added to the devices to prevent the passage of contamination and other agents.

SUMMARY OF THE INVENTION

The embodiments described herein can be used to control the level of humidity in a gas. The effective addition of humidity to the gas is achieved by providing an extremely large surface area for contact and molecular transfer between the water and the gas, without any membrane or barrier separating the two media.

One aspect of the invention is directed to a first gas humidifier. The first gas humidifier comprises a field of at least one million hydrophobic nanotubes with diameters between 1 and 100 nm with spaces between the nanotubes though which gas can travel, with voids in the field positioned to form a plurality of liquid flow channels, each of which is surrounded by the nanotubes. The channels are wide enough for liquid water to pass through, and the nanotubes adjacent to the channels are spaced close enough to each other to prevent liquid water from escaping the channels. The first gas humidifier also comprises a gas pathway that passes through spaces between the nanotubes and extends from an input to the field of nanotubes to an output from the field of nanotubes; a water container having an interior that is in fluid communication with the channels; a humidity sensor located downstream of the gas pathway so as to measure humidity of gas that has passed through the field of nanotubes; and a control system configured to receive humidity data from the humidity sensor and to adjust a flow rate of gas through the gas pathway in response to the humidity data so as to achieve a set level of gas humidity.

In some embodiments of the first gas humidifier, the nanotubes comprise vertically aligned carbon nanotubes.

Some embodiments of the first gas humidifier further comprise a heating element disposed in sufficient proximity to the gas pathway to heat gas as it flows along the gas pathway; and a temperature sensor disposed at a location where the temperature sensor is able to measure a temperature of the gas flowing within the gas pathway, or a temperature that is indicative thereof. In these embodiments, the control system is further configured to receive temperature data from the temperature sensor and to control operation of the heating element in response to the temperature data.

In some embodiments of the first gas humidifier, the nanotubes are electrically conductive, and the gas humidifier further comprises an upper layer of electrically conductive material connected to upper ends of the nanotubes; and a lower layer of electrically conductive material connected to lower ends of the nanotubes. The upper and lower layers are arranged with respect to the nanotubes (a) so that application of a voltage across the upper layer and the lower layer will cause an electrical current to flow through the nanotubes and (b) so as not to block water from entering the channels.

In some embodiments of the first gas humidifier, the field of nanotubes is contained within a cartridge. The cartridge has (a) an input port in fluid communication with the input to the field of nanotubes, and (b) an output port in fluid communication with the output from the field of nanotubes. A coating that prevents gas from escaping is disposed above and below the field of nanotubes, and the channels have top and bottom openings that are not blocked by the coating. Optionally, in these embodiments, the water container may have a water inlet configured to receive water. Optionally, these embodiments may further comprise a temperature sensor positioned in thermal contact with the water in the cartridge.

In some embodiments of the first gas humidifier, the input to the field of nanotubes and the output from the field of nanotubes are disposed on opposite sides of the field.

In some embodiments of the first gas humidifier, the gas humidifier includes at least two discrete banks of nanotubes. Each of the banks has a field of at least one million hydrophobic nanotubes with diameters between 1 and 100 nm with spaces between the nanotubes through which gas can travel, with voids in the field positioned to form a plurality of liquid flow channels, each of which is surrounded by the nanotubes. The channels are wide enough for liquid water to pass through, and the nanotubes adjacent to the channels are spaced close enough to each other to prevent liquid water from escaping the channels. Each of the banks also has a gas pathway that passes through spaces between the nanotubes and extends from an input to the field of nanotubes to an output from the field of nanotubes. These embodiments further comprise a system gas flow conduit comprising at least two branches arranged in parallel to provide gas to respective banks; and a system of flow control valves arranged to individually permit or prevent flow of gas through the at least two banks. In these embodiments, the control system is further configured to control the flow control valves in response to humidity data received from the humidity sensor, thereby adjusting the number of banks through which gas flows, and hence total water/gas exchange surface area, to achieve a set level of humidity.

Another aspect of the invention is directed to a second gas humidifier. The second gas humidifier comprises a field of at least one million hydrophobic nanotubes with diameters between 1 and 100 nm with spaces between the nanotubes though which gas can travel, with voids in the field positioned to form a plurality of liquid flow channels, each of which is surrounded by the nanotubes. The channels are wide enough for liquid water to pass through, and the nanotubes adjacent to the channels are spaced close enough to each other to prevent liquid water from escaping the channels. The second gas humidifier also comprises a gas pathway that passes through spaces between the nanotubes and extends from an input to the field of nanotubes to an output from the field of nanotubes; and a water container having an interior that is in fluid communication with the channels. The field of nanotubes is contained within a cartridge. The cartridge has (a) an input port in fluid communication with the input to the field of nanotubes, and (b) an output port in fluid communication with the output from the field of nanotubes. A coating that prevents gas from escaping is disposed above and below the field of nanotubes, and the channels have top and bottom openings that are not blocked by the coating.

In some embodiments of the second gas humidifier, the nanotubes comprise vertically aligned carbon nanotubes. In some embodiments of the second gas humidifier, the water container has a water inlet configured to receive water.

In some embodiments of the second gas humidifier, the nanotubes are electrically conductive, and the second gas humidifier further comprises an upper layer of electrically conductive material connected to upper ends of the nanotubes; and a lower layer of electrically conductive material connected to lower ends of the nanotubes. In these embodiments, the upper and lower layers are arranged with respect to the nanotubes (a) so that application of a voltage across the upper layer and the lower layer will cause an electrical current to flow through the nanotubes and (b) so as not to block water from entering the channels.

Another aspect of the invention is directed to a first method for humidifying gas. The first method comprises providing a field of at least one million hydrophobic nanotubes with diameters between 1 and 100 nm arranged with spaces between the nanotubes though which gas can travel, with voids in the field positioned to form a plurality of liquid flow channels, each of which is surrounded by the nanotubes. The channels are wide enough for liquid water to pass through in a direction that is parallel to the nanotubes, and the nanotubes adjacent to the channels are spaced close enough to each other to prevent liquid water from escaping the channels. The first method also comprises providing water within the channels in the field of nanotubes; and causing a gas to pass through spaces between the nanotubes from an input to the field of nanotubes to an output from the field of nanotubes. Humidification of the gas occurs by transfer of molecules from the water located within the channels to the gas. A humidity level of gas that has passed through the field of nanotubes is measured. And the rate of flow of gas into the field of nanotubes is regulated based on the measured humidity level.

Some instances of the first method further comprise heating the gas as it passes through the field of nanotubes. Some instances of the first method further comprise passing an electrical current vertically through the field of nanotubes. Some instances of the first method further comprise adjusting a total area of molecular transfer from the water to the gas so as to achieve a set level of humidity.

BRIEF DESCRIPTION OF THE DRAWINGS

FIG. 3B depicts a cross section view of the FIG. 3A embodiment.

FIGS. 3C-3D depict two different section views of the FIG. 3A embodiment.

Various embodiments are described in detail below with reference to the accompanying drawings, wherein like reference numerals represent like elements.

DESCRIPTION OF THE PREFERRED EMBODIMENTS

This application describes a new approach for humidifying a gas (e.g., a gas being provided for patient inspiration).

In all the embodiments described herein, humidification of a gas is achieved in one or more "plates" made using nanotubes.

Each of the plates may be formed from a very large number (e.g., millions or billions) of hydrophobic nanotubes with diameters between 1 and 100 nm. In some preferred embodiments, the nanotubes are vertically aligned carbon nanotubes, which are highly hydrophobic. Single wall and/or multi-wall nanotubes may be used. The nanotubes are positioned in a "field" with a large number (e.g., thousands or hundreds of thousands) of voids in that field that define channels through which water can pass. These channels are referred to herein as "liquid flow channels" or "channels." The liquid flow channels are wide enough (e.g., between 2 and 500 µm) for the water to flow through, and the nanotubes are spaced close enough together to retain the water within the liquid flow channels, due to the hydrophobic nature of the carbon nanotubes and the surface tension of the water.

Figure 1A:
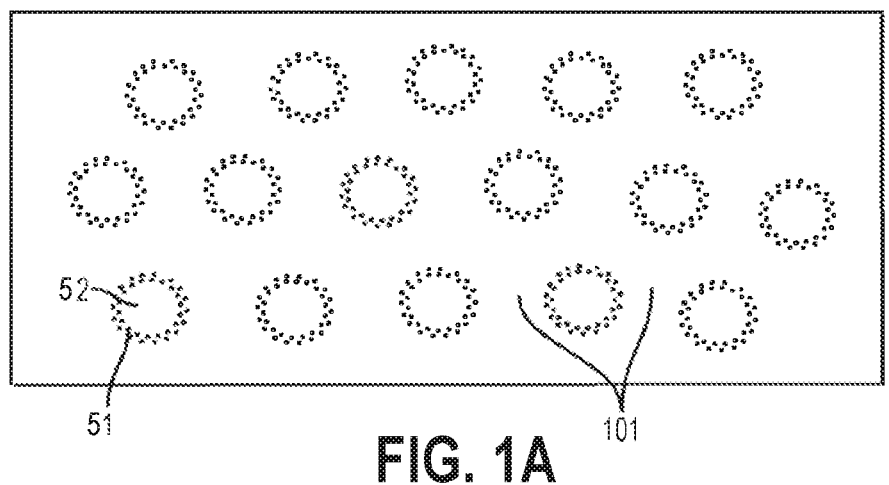
FIGS. 1A-IC depict three alternative approaches for laying out a field of nanotubes to form channels.
Figure 1B:
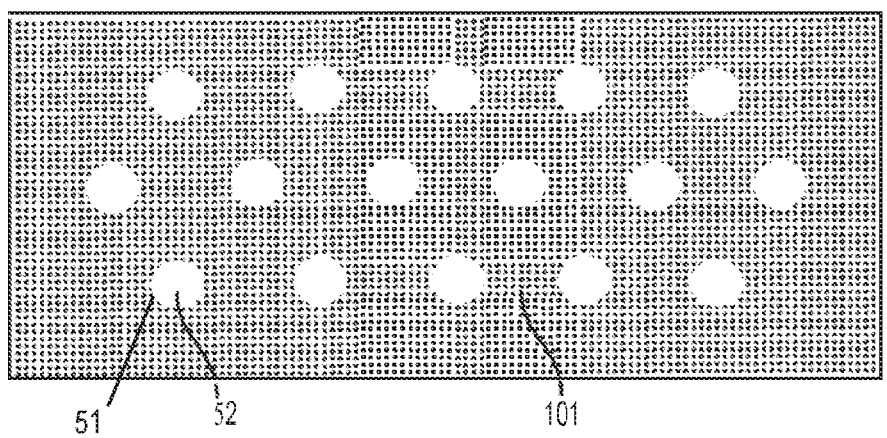
Figure 1C:
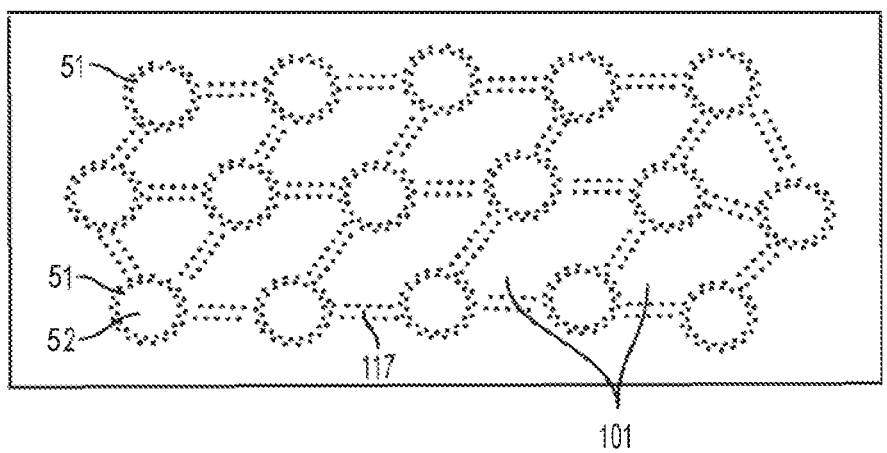

FIGS. 1A-1C depict three example approaches for laying out the field of nanotubes 51 to define the channels 52. In each of these examples, the depicted view is a cross section through the channels 52 and the nanotubes 51. In the FIG. 1A approach, the nanotubes 51 are laid out in a pattern of rings so that the inner boundary of each ring defines a channel 52. In the FIG. 1B approach, the nanotubes 51 are laid out like a carpet (e.g., a regular two dimensional matrix), and there are voids in the field of nanotubes 51 that define the channels 52. The FIG. 1C approach is similar to the approach depicted in FIG. 1A, except that additional nanotubes 51 are added to provide structural support. The additional nanotubes 51 may be configured, e.g., to form support bridges 117, as shown in FIG. 1C, but alternative layouts for the additional nanotubes 51 may be used instead. The layout of the additional nanotubes 51 may be selected to provide structural strength without unduly increasing the resistance to air flow. A wide variety of alternative approaches for laying out the nanotubes 51 to define the channels 52 can also be used.

In some embodiments, the nanotubes 51 may be free standing; held together by Van der Waals forces; or mounted on a base or substrate (e.g., a plate of alumina, silicon, etc.). When the nanotubes 51 are mounted on a substrate, an opening in the substrate is provided beneath each of the channels 52. The field of nanotubes and the channels 52 therein may be constructed as described in U.S. Pat. Nos. 9,138,522 and 9,827,534, each of which is incorporated herein by reference in its entirety.

Alternatively, each of the plates may be formed from a very large number (e.g., millions or billions) of interconnected nanotubes, with interconnections between the nanotubes that are sufficient to hold the plate together without requiring a substrate (in which case the substrate on which the nanotubes are originally grown can be removed). Examples of this variety of plate are described in "c-VACNT™ Enabled Fluid Reactor Innovations" by K. Strobl et al. (June 2019); "Vertically aligned carbon nanotube arrays as a thermal interface material" by L. Ping et al., APL Mater. 7, 020902 (2019); doi: 10.1063/1.5083868 (February 2019); and in "Transfer of vertically aligned carbon nanotube arrays onto flexible substrates for gecko-inspired dry adhesive application" by Yang Li et al., RSC Advances, Issue 58 (May 2015). As in the previous variation, when this variation of gas-exchange plate is used, a large number (e.g., thousands or hundreds of thousands) of preferably identical vertical liquid flow channels pass through the field of nanotubes.

Figure 2:
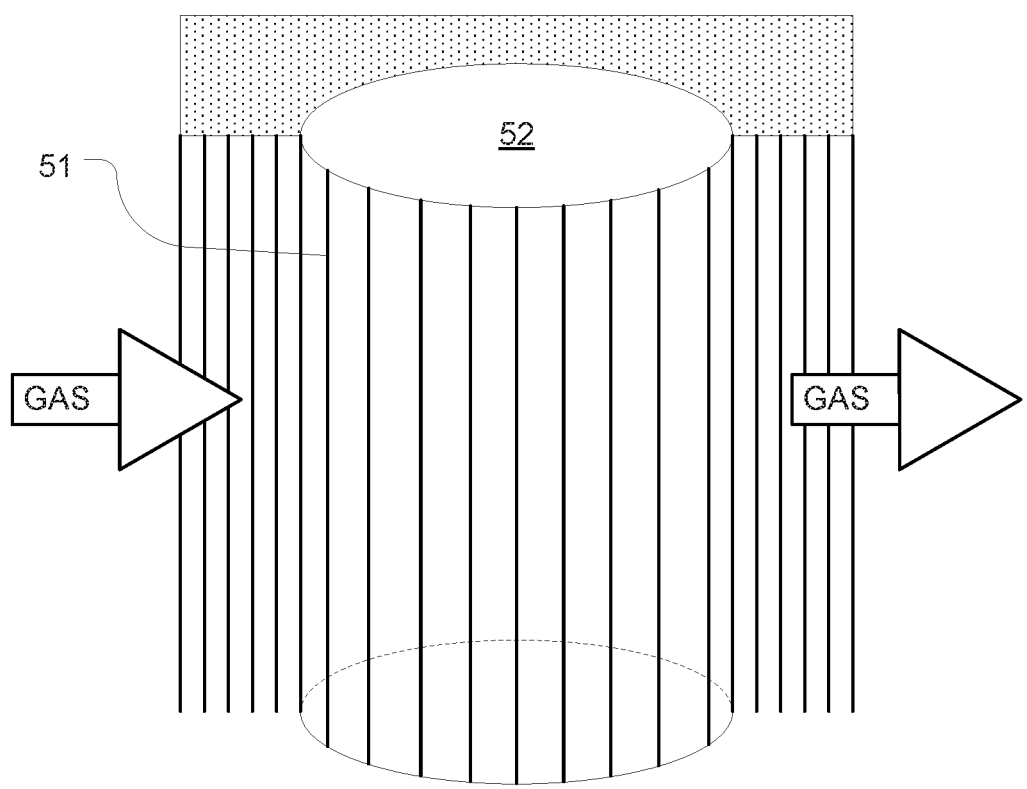
FIG. 2 is a schematic diagram illustrating a channel formed as a void within a field of densely packed nanotubes, with gas passing through the field of nanotubes.

It is important to note that, whichever variety of plate is used, the channels 52 have no coating or membrane to keep the water from escaping the channel. However, due to the high density (i.e., the close spacing) of the hydrophobic nanotubes 51 surrounding the channels 52 and the high surface tension of water, when water occupies or flows in the channels, it will not leak out of the channels into the gas flow/diffusion region. In other words, the nanotubes 51 surrounding the channel 52 form a virtual boundary for the water flow. The interaction between the water and the gas (e.g., the evaporation of the water into the gas) occurs at this virtual boundary. This arrangement is illustrated in FIG. 2, which depicts a side view of one of the channels 52, as seen from immediately outside the channel. The channel 52 is surrounded by nanotubes 51.

Whichever variety of plate is used, the water will travel through the liquid flow channels, while the gas that will exchange molecules with the water permeates the spaces between the nanotubes (analogous to the way air permeates through a forest of trees). Because the nanotubes in the field are densely packed, they can present significant resistance to horizontal flow of gas. So to ensure that the gas reaches the liquid flow channels, conduits that are free of nanotubes may optionally be included in the plate in some embodiments. In these embodiments, gas will permeate to the boundaries of the liquid flow channels by the combination of gas flowing through the conduits and diffusion from the conduits to nearby liquid flow channels.

Figure 3A:
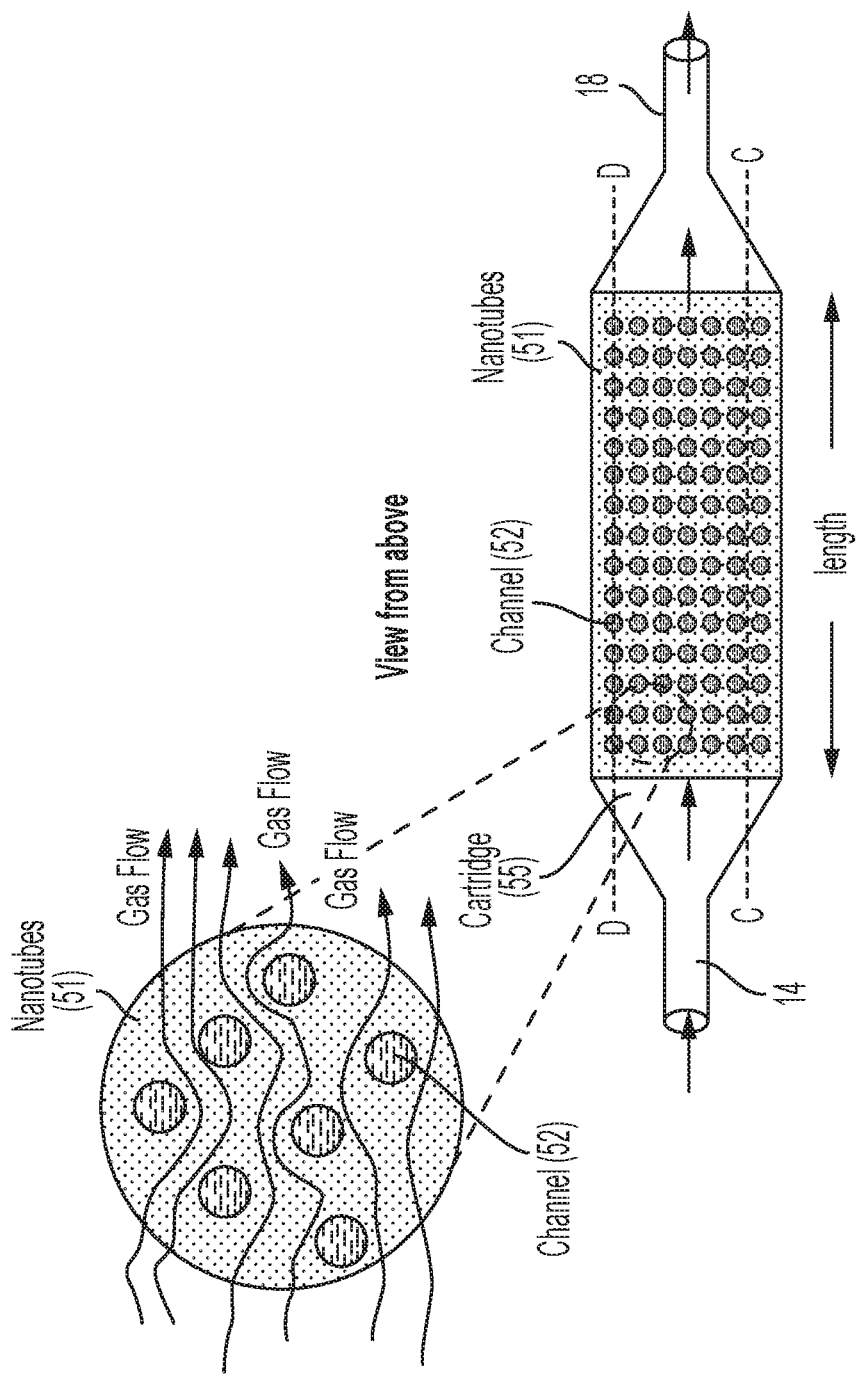
FIG. 3A depicts a plan section view of an embodiment of a humidifier.
Figure 4:
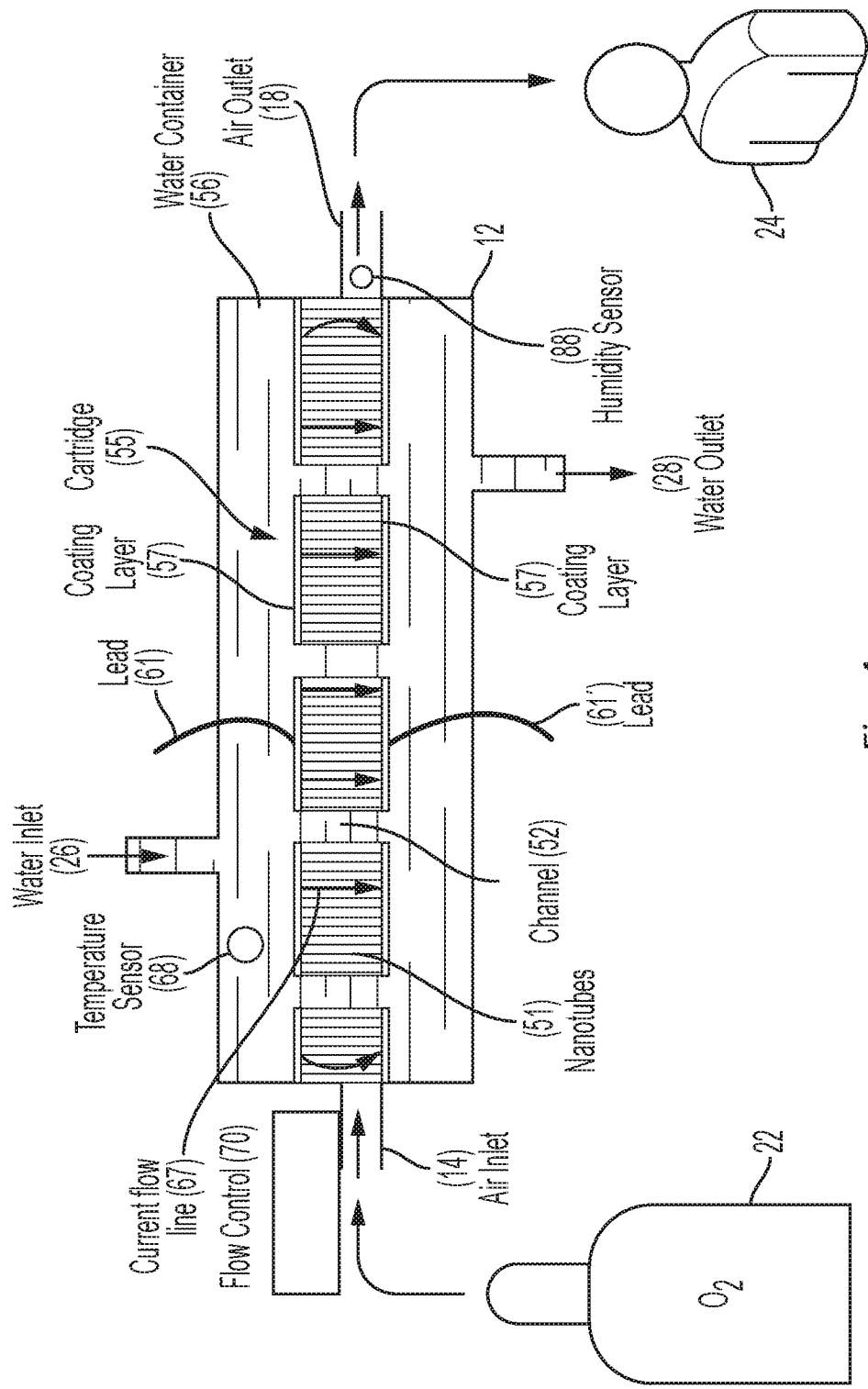
FIG. 4 depicts the FIG. 3A embodiment with additional components that are not visible in FIGS. 3A-3D.

FIGS. 3-4 depict a first embodiment of a humidifier designed to effectively humidify a gas. In this embodiment, gas travels from left to right through the field of nanotubes 51, from one side of the field to the opposite side of the field, flowing and/or diffusing through and restricted to the interstitial spaces between the nanotubes 51. In addition, water fills the channels 52, which extend in the vertical direction of the field of nanotubes 51 (i.e., perpendicular to the page in FIG. 3A and vertical in FIGS. 3B-3D). Thus, the areas along which the gas travels, through the field of nanotubes 51, form at least part of a gas pathway, and the channels 52 form at least part of a water pathway.

The field of nanotubes 51 includes at least one million (and in some preferred embodiments at least one billion) hydrophobic nanotubes with diameters between 1 and 100 nm with spaces between the nanotubes though which gas can travel. Voids in the field are positioned to form a plurality of liquid flow channels 52, each of which is surrounded by the nanotubes 51. The channels 52 are wide enough for liquid water to pass through, and the nanotubes 51 adjacent to the channels 52 are spaced close enough to each other to prevent liquid water from escaping the channels.

This arrangement provides an extremely large surface area for contact and molecular transfer between the water (in the channels 52) and the gas traveling along the gas pathway, i.e., permeating through the field of nanotubes 51, and surrounding the virtual boundaries of the channels 52. For example, for a field that is 2 mm in vertical height, with channels 52 having a radius of 25 microns spaced 25 microns apart, there are about 20,000 channels 52 per square centimeter, and the total surface area of these 20,000 channels 52—i.e., area across which water molecules can be transferred to the gas—is about 30 square centimeters. (As water molecules evaporate, and thus are transferred from the channels 52 to the gas, they will be replaced by water from the water container 56.)

FIG. 3A depicts the nanotubes 51 laid out in a carpet pattern, with the voids within the field defining the channels 52. In some preferred embodiments, the vertical (i.e., perpendicular to the page) height of the nanotubes 51 is 1-2 mm. The nanotubes 51 have diameters in the order of 1-100 nm, and in some preferred embodiments, the nanotubes' diameter is 2-10 nm. The distances between the centers of the nanotubes 51 can be from 20-500 nm, and in some preferred embodiments, the distance between the centers of the nanotubes is 100-300 nm. In some embodiments, the diameter of the channels 52 is between 2 and 500 µm, and in some embodiments the diameter is between 5 and 20 µm. In the illustrated embodiment, the nanotubes 51 within the field (i.e., outside the voids) are arranged as a two dimensional matrix. But in alternative embodiments, different layouts for the nanotubes 51 may be used (e.g., as described above in connection with FIGS. 1A-IC)

In all embodiments, the optimum distance between the nanotube centers will be related to the nanotube diameter, so that the nanotubes do not end up too far away from each other for the surface tension to retain the water in the channels 52. For example, when thinner nanotubes are used, the nanotubes should preferably be packed more closely together. Preferably, the spacing between nanotubes will be not more than a few diameters of the nanotubes, and in some preferred embodiments will be on the order of 1 diameter. For example, if nanotubes with 10 nm diameter are used, the nanotubes may be spaced on centers of about 20 nm, which would mean that the spacing between adjacent nanotubes would be around one diameter. But if nanotubes with 20 nm diameter are used, the nanotubes should be spaced further apart, e.g., on centers of about 40 nm. In some preferred embodiments, a suitable relationship between the nanotube diameter and the nanotube spacing is to space the nanotubes on centers that are between 1.5 times the diameter of the nanotube and 5 times the diameter of the nanotube. For example, if nanotubes with a diameter of 10 nm are used, the nanotubes would be spaced on centers between 15 and 50 nm. In other embodiments, the nanotubes are spaced centers between 1 times and 10 times the diameter of the nanotubes, or even between 0.5 times and 20 times the diameter of the nanotubes. Note that the density of the nanotubes as well as the density of the channels determine both (a) the exchange capacity and (b) the resistance to gas flow, and both of these parameters should be considered in selecting the layout and spacing of the nanotubes. As noted above, optional gas-flow conduits may be incorporated into the plate to improve the delivery of gas to the vicinity of the channels 52.

As best seen in FIGS. 3C, 3D, and 4, the field of nanotubes 51 is coated at both its top and bottom surfaces, except for the openings of the channels 52 by a thin coating layer 57. This coating layer 57 may be formed, for example, by vapor deposition. This coating layer 57 prevents gas from escaping from the top or bottom of the field of nanotubes 51 (when viewed in the orientation depicted in FIG. 4). In some preferred embodiments, the coating layer 57 is made of an electrically conductive material (e.g., carbon).

In some preferred embodiments, including the embodiment illustrated in FIGS. 3-4, the field of nanotubes is provided in the form of a cartridge 55, which may optionally be disposable. The cartridge has an input port 14 in fluid communication with the input to the field of nanotubes, and an output port 18 in fluid communication with the output from the field of nanotubes.

Turning now to FIG. 4, during use, the cartridge 55 is positioned in a container 56 that is filled with water (e.g., via water inlet 26). Optionally, the container 56 may also have an outlet 28, which can be opened or closed as needed to assist filling the container 56 and the channels 52 with water, prevent the formation of bubbles, and flush out the container 56. Because the coating layer 57 does not cover the openings of the channels 52 (see FIGS. 3B and 4), those channels 52 will remain in fluid communication with the interior of the water container 56, so that water from the interior of container 56 will enter the channels 52. The gas that is to be humidified exits the gas supply 22 and enters the cartridge 55 via input port 14 (which is the upstream end of the gas pathway). The gas interacts with the water in the channels 52 and becomes humidified, and eventually exits the cartridge 55 via the output port 18 (which is the downstream end of the gas pathway). From there, the humidified gas is provided to the patient 24.

Preferably, the relative humidity of the gas exiting the humidifier can be controlled by changing the amount of evaporation. This can be achieved using the output of a humidity sensor 88 (positioned, e.g., at a downstream end of the gas pathway) to control a flow controller 70 using a standard feedback loop. The control is achieved, for example, by providing humidity data as measured by the humidity sensor 88 to the flow controller 70 and adjusting the flow rate of the gas (e.g., using a needle valve or other regulator to adjust the rate at which gas exits the supply 22) to achieve a desired level of humidity. The flow rate of the gas, in turn, affects the evaporation rate of the water and hence the level of humidification. In alternative embodiments, the level of humidification could be adjusted by controlling the amount of water that flows into the system.

Figure 5:
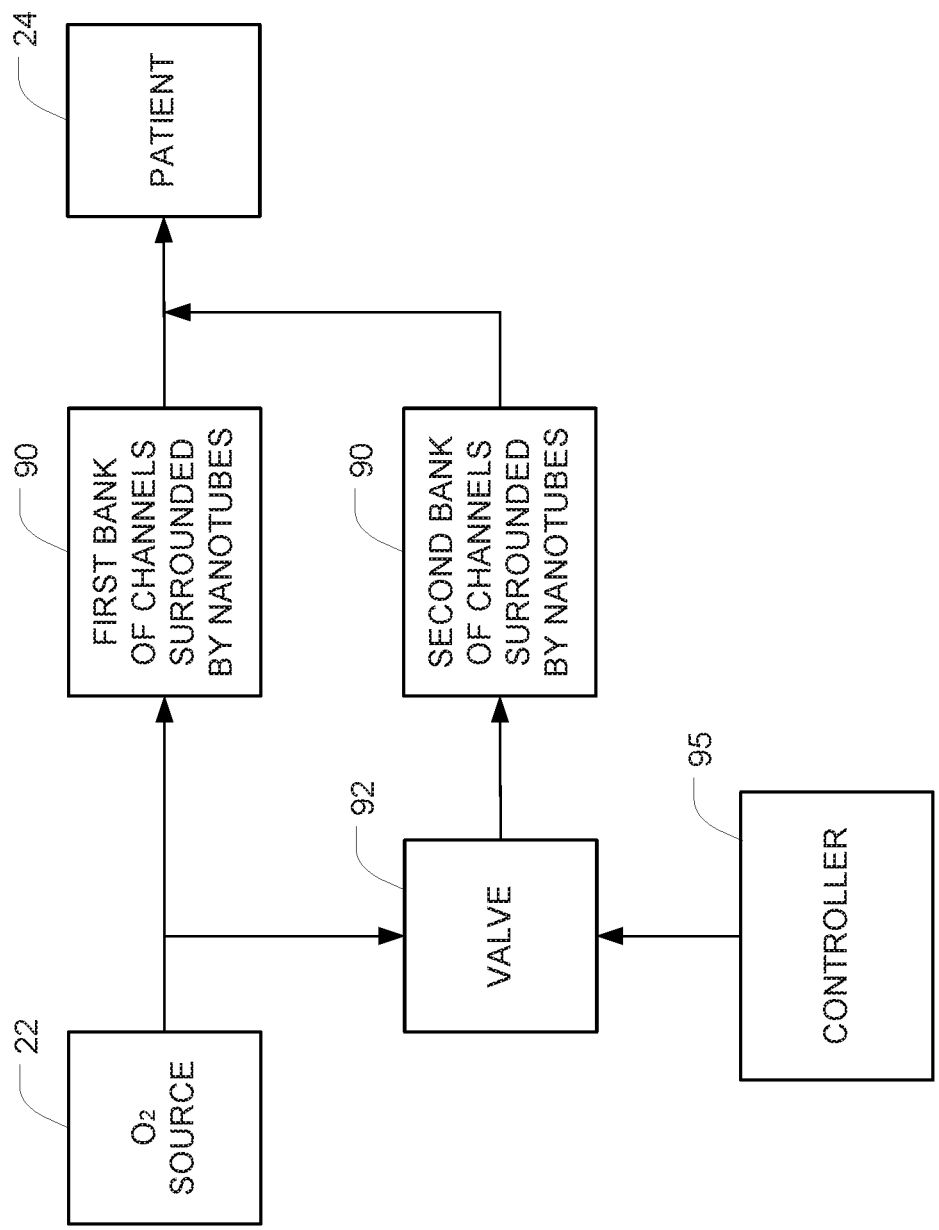
FIG. 5 depicts an alternative embodiment that provides a plurality of banks of humidification.

FIG. 5 depicts another configuration in which the level of humidification can be controlled by varying the total surface area over which humidifying transfer of water molecules to the gas takes place. This can be accomplished by providing a plurality of "banks" 90 of liquid flow channels surrounded by nanotubes, which are arranged in parallel. The construction of each of these banks 90 may be similar to the construction of the cartridge described above in connection with FIG. 3A, and these banks are arranged so that water fills the liquid flow channels in each of the banks. Each bank 90 is supplied with gas by a feeder conduit, and the feeder conduits to these banks 90 can be opened or closed individually by one or more valves 92 that are operated by a controller 95. Thus, as more humidification is needed, the controller 95 will open more of the valves 92, so that the gas can flow through more banks of liquid flow channels surrounded by nanotubes to absorb more water molecules.

An optional additional function that the humidifier can provide is to heat the gas to a desired temperature, e.g., 37° C. in the case of oxygen used for ventilation. One example of a suitable configuration that may be used to heat the gas is best seen in FIGS. 3C, 3D, and 4. This arrangement is particularly suited to those embodiments where the multiplicity of nanotubes is arranged like a carpet-like field with voids therein to form the liquid flow channels (as depicted in FIGS. 1B and 3A).

As noted above, the field of nanotubes 51 is coated at both its top and bottom surfaces, except for the openings of the channels 52, by a thin coating layer 57, which may optionally be made of an electrically conductive material (e.g., carbon). The embodiments that use carbon nanotubes combined with an electrically conductive coating layer 57 are particularly advantageous because carbon nanotubes are conductive and a large number of carbon nanotubes span the distance between the upper and lower coating layers 57. As a result, heating in this embodiment can be accomplished by applying a voltage between the upper and lower coating layers 57 via the leads 61, 61'. The applied voltage will cause a current to flow through the carbon nanotubes, which will generate heat. As the electric resistance between the upper and lower surfaces of a typical nanotube carpet is about 10Ω per an area of 1 cm², a 10 cm² carpet would function as a 1 Watt heater when activated by a 1 Volt potential difference. Changing the voltage will change the amount of heat that is generated.

Because the gas is flowing within the cartridge 55, and water from the water container 56 runs through the channels 52 in the cartridge 55, and because the cartridge 55 is made predominantly of carbon (which has an extremely high thermal conductivity), the temperature of the flowing gas can be adjusted to a desired level by heating or cooling the water in the water container 56 (which engulfs the cartridge 55). The temperature of this water is monitored by a conventional temperature sensor 68, and heat is applied as required (e.g., using any of the approaches described herein) until the water temperature reaches a desired level. For example, the amount of heat that is added to the system can be controlled by controlling the voltage that is applied to the leads 61 or by controlling the current that passes through those leads. A simple feedback loop and voltage controller can easily maintain the water temperature—and hence the gas temperature—at any desired level.

In alternative embodiments, a different approach for heating the gas may be used. For example, a separate resistive heater (not shown) may be used to heat the water in the container 56.

In any of the embodiments that provide heating, the humidity of the gas can also be adjusted by heating the gas as necessary to achieve a desired level of humidity. This is because warmer gas is able to hold more water vapor than colder gas. In these embodiments the humidity can be controlled by measuring the humidity using a humidity sensor 88, measuring the temperature using temperature sensor 68, and controlling a heater (e.g., the heater formed by the conductive coating 57 and the nanotubes 51, as described above) to heat the gas in order to obtain the desired level of humidity.

In addition to serving to humidify and optionally control the temperature of the supplied gas, the humidifier can also filter the gas by serving as a particle filter. Carpet-like fields of nanotubes are known to be excellent particle filters. As the distances between the nanotubes are in the 20-500 nm range, and the flowing/diffusing gas passes horizontally through the carpet-like field of millions of such tubes, any particle or contamination that accompanies the gas is trapped in the carpet. The filtration prevents contaminants such as bacteria and viruses from reaching the lungs.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

I claim:

1. A gas humidifier, comprising:
   a field of at least one million hydrophobic nanotubes with diameters between 1 and 100 nm with spaces between the nanotubes though which gas can travel, with voids in the field positioned to form a plurality of liquid flow channels, each of which is surrounded by the nanotubes, wherein the channels are wide enough for liquid water to pass through, and wherein the nanotubes adjacent to the channels are spaced close enough to each other to prevent liquid water from escaping the channels;
   a gas pathway that passes through spaces between the nanotubes and extends from an input to the field of nanotubes to an output from the field of nanotubes;
   a water container having an interior that is in fluid communication with the channels;
   a humidity sensor located downstream of the gas pathway so as to measure humidity of gas that has passed through the field of nanotubes; and
   a control system configured to receive humidity data from the humidity sensor and to adjust a flow rate of gas through the gas pathway in response to the humidity data so as to achieve a set level of gas humidity.

2. The gas humidifier of claim 1, wherein the nanotubes comprise vertically aligned carbon nanotubes.

3. The gas humidifier of claim 1, further comprising:
   a heating element disposed in sufficient proximity to the gas pathway to heat gas as it flows along the gas pathway; and
   a temperature sensor disposed at a location where the temperature sensor is able to measure a temperature of the gas flowing within the gas pathway, or a temperature that is indicative thereof,
   wherein the control system is further configured to receive temperature data from the temperature sensor and to control operation of the heating element in response to the temperature data.

4. The gas humidifier of claim 1, wherein the nanotubes are electrically conductive and further comprising:
   an upper layer of electrically conductive material connected to upper ends of the nanotubes; and
   a lower layer of electrically conductive material connected to lower ends of the nanotubes,
   wherein the upper and lower layers are arranged with respect to the nanotubes (a) so that application of a voltage across the upper layer and the lower layer will cause an electrical current to flow through the nanotubes and (b) so as not to block water from entering the channels.

5. The gas humidifier of claim 1, wherein the field of nanotubes is contained within a cartridge, the cartridge having (a) an input port in fluid communication with the input to the field of nanotubes, and (b) an output port in fluid communication with the output from the field of nanotubes, wherein a coating that prevents gas from escaping is disposed above and below the field of nanotubes, and wherein the channels have top and bottom openings that are not blocked by the coating.

6. The gas humidifier of claim 5, wherein the water container has a water inlet configured to receive water.

7. The gas humidifier of claim 5, further comprising a temperature sensor positioned in thermal contact with the water in the cartridge.

8. The gas humidifier of claim 1, wherein the input to the field of nanotubes and the output from the field of nanotubes are disposed on opposite sides of the field.

9. The gas humidifier of claim 1, wherein the gas humidifier includes:
   at least two discrete banks of nanotubes, each of the banks having (a) a field of at least one million hydrophobic nanotubes with diameters between 1 and 100 nm with spaces between the nanotubes though which gas can travel, with voids in the field positioned to form a plurality of liquid flow channels, each of which is surrounded by the nanotubes, wherein the channels are wide enough for liquid water to pass through, and wherein the nanotubes adjacent to the channels are spaced close enough to each other to prevent liquid water from escaping the channels and (b) a gas pathway that passes through spaces between the nanotubes and extends from an input to the field of nanotubes to an output from the field of nanotubes;

a system gas flow conduit comprising at least two branches arranged in parallel to provide gas to respective banks; and a system of flow control valves arranged to individually permit or prevent flow of gas through the at least two banks, wherein the control system is further configured to control the flow control valves in response to humidity data received from the humidity sensor, thereby adjusting the number of banks through which gas flows, and hence total water/gas exchange surface area, to achieve a set level of humidity.

10. A gas humidifier, comprising:

a field of at least one million hydrophobic nanotubes with diameters between 1 and 100 nm with spaces between the nanotubes though which gas can travel, with voids in the field positioned to form a plurality of liquid flow channels, each of which is surrounded by the nanotubes, wherein the channels are wide enough for liquid water to pass through, and wherein the nanotubes adjacent to the channels are spaced close enough to each other to prevent liquid water from escaping the channels;

a gas pathway that passes through spaces between the nanotubes and extends from an input to the field of nanotubes to an output from the field of nanotubes; and a water container having an interior that is in fluid communication with the channels, wherein the field of nanotubes is contained within a cartridge, the cartridge having (a) an input port in fluid communication with the input to the field of nanotubes, and (b) an output port in fluid communication with the output from the field of nanotubes, wherein a coating that prevents gas from escaping is disposed above and below the field of nanotubes, and wherein the channels have top and bottom openings that are not blocked by the coating.

11. The gas humidifier of claim 10, wherein the nanotubes comprise vertically aligned carbon nanotubes.

12. The gas humidifier of claim 10, wherein the water container has a water inlet configured to receive water.

13. The gas humidifier of claim 10, wherein the nanotubes are electrically conductive and further comprising:

an upper layer of electrically conductive material connected to upper ends of the nanotubes; and a lower layer of electrically conductive material connected to lower ends of the nanotubes, wherein the upper and lower layers are arranged with respect to the nanotubes (a) so that application of a voltage across the upper layer and the lower layer will cause an electrical current to flow through the nanotubes and (b) so as not to block water from entering the channels.

14. A method for humidifying a gas, comprising:

providing a field of at least one million hydrophobic nanotubes with diameters between 1 and 100 nm arranged with spaces between the nanotubes though which gas can travel, with voids in the field positioned to form a plurality of liquid flow channels, each of which is surrounded by the nanotubes, wherein the channels are wide enough for liquid water to pass through in a direction that is parallel to the nanotubes, and wherein the nanotubes adjacent to the channels are spaced close enough to each other to prevent liquid water from escaping the channels;

providing water within the channels in the field of nanotubes;

causing a gas to pass through spaces between the nanotubes from an input to the field of nanotubes to an output from the field of nanotubes, wherein humidification of the gas occurs by transfer of molecules from the water located within the channels to the gas;

measuring a humidity level of gas that has passed through the field of nanotubes; and regulating a rate of flow of gas into the field of nanotubes based on the measured humidity level.

15. The method of claim 14, further comprising heating the gas as it passes through the field of nanotubes.

16. The method of claim 14, further comprising passing an electrical current vertically through the field of nanotubes.

17. The method of claim 14, further comprising adjusting a total area of molecular transfer from the water to the gas so as to achieve a set level of humidity.

* * * * *